(12) United States Patent
Norén

(10) Patent No.: US 7,058,448 B2
(45) Date of Patent: Jun. 6, 2006

(54) DUAL CHAMBER PACING SYSTEM WITH A MODE SWITCH

(75) Inventor: Kjell Norén, Solna (SE)

(73) Assignee: St. Jude Medical AB, Jarfalla (SE)

( * ) Notice: Subject to any disclaimer, the term of this patent is extended or adjusted under 35 U.S.C. 154(b) by 373 days.

(21) Appl. No.: 10/478,144

(22) PCT Filed: Sep. 23, 2002

(86) PCT No.: PCT/SE02/01722

§ 371 (c)(1),
(2), (4) Date: Nov. 18, 2003

(87) PCT Pub. No.: WO03/061760

PCT Pub. Date: Jul. 31, 2003

(65) Prior Publication Data

US 2004/0133245 A1    Jul. 8, 2004

(30) Foreign Application Priority Data

Jan. 17, 2002  (SE)  .................................... 0200121

(51) Int. Cl.
*A61N 1/362*  (2006.01)

(52) U.S. Cl. .......................................................... 607/9
(58) Field of Classification Search ................... 607/9, 607/14
See application file for complete search history.

(56) References Cited

U.S. PATENT DOCUMENTS

| 4,802,483 A | 2/1989 | Lindgren |
| 5,309,919 A | 5/1994 | Snell et al. |
| 5,713,938 A | 2/1998 | Chiang et al. |
| 5,893,882 A | 4/1999 | Peterson et al. |

FOREIGN PATENT DOCUMENTS

EP    1 048 322    4/2000

OTHER PUBLICATIONS

"A New Automode Switch Algorithm for Supraventricular Tachycardias," Levine et al., PACE, vol. 17, Nov. 1994, Part II, pp. 1895-1899.

*Primary Examiner*—Scott M. Getzow
(74) *Attorney, Agent, or Firm*—Schiff Hardin LLP

(57) ABSTRACT

A dual chamber pacing system normally operates in an atrial synchronized mode, and includes a mode switch that switches the pacing mode to a non-atrial synchronized ventricular stimulating mode in response to the detection of an atrial tachyarrhythmia, and switches the pacing mode back to the atrial synchronized mode in response to, or after a preset time following, detection of cessation of the atrial tachyarrhythmia. A mode switch supervising circuit includes a counter that accumulates an amount of mode switches from a starting point, and supplies the accumulated amount to a comparator, wherein the accumulated amount is compared to a predetermined mode switch amount threshold. The mode switch supervising circuit controls the mode switch to lock the pacing mode to the non-atrial synchronized ventricular stimulating mode for at least a predetermined time period in response to the mode switch amount exceeding the amount threshold.

6 Claims, 1 Drawing Sheet

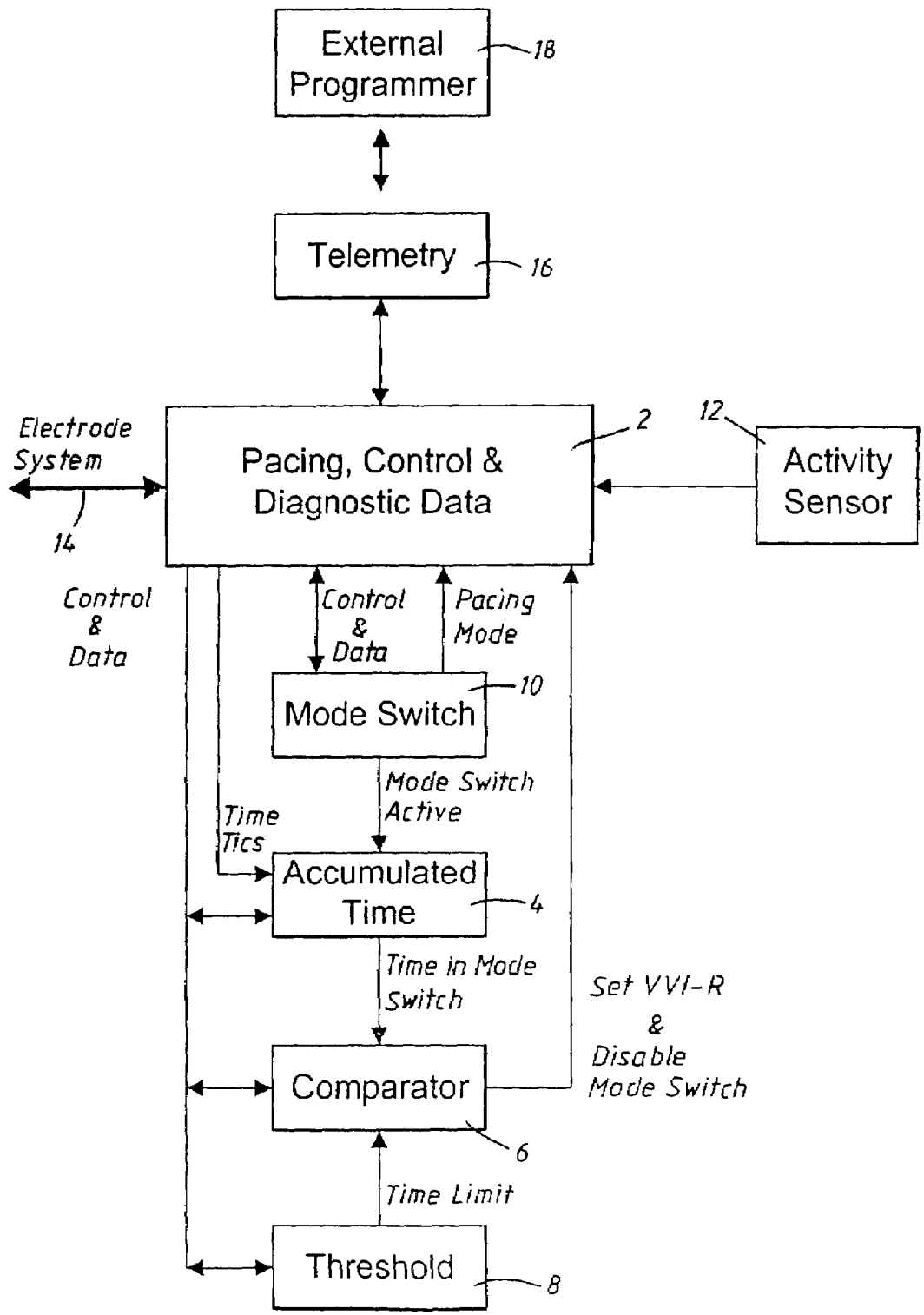

DUAL CHAMBER PACING SYSTEM WITH A MODE SWITCH

BACKGROUND OF THE INVENTION

1. Field of the Invention

The present invention relates to a dual chamber pacing system normally operating in an atrial synchronized mode of the type having a mode switch to switch the pacing mode to a non-atrial synchronized ventricle stimulating mode in response to the detection of an atrial tachyarrhythmia and to switch the pacing mode back to the atrial synchronized mode in response to or after a preset time of the detection of ceased atrial tachyarrhythmia.

2. Description of the Prior Art

A dual chamber pacing system, i.e. a DDD-R system, should not track the atrial activity during atrial tachyarrhythmia including atrial fibrillation (AF). The pacing mode should in this case be changed to VVI-R. In U.S. Pat. No. 5,893,882 a pacemaker is described that is provided with a mode switching feature adapted to stabilize the ventricular heart rate during atrial fibrillation. In response to detection of atrial fibrillation the device therefore switches into a non-atrial synchronized ventricular rate stabilization pacing mode. The device remains in this mode of operation as long as the atrial fibrillation remains and during a preset time thereafter.

A problem arises for a patient having a pacemaker with a mode switching feature of this known kind, if the tachyarrhythmia or AF changes from paroxysmal, i.e. intermittent, seizures to a chronically, i.e. permanent, state between the follow-up tests of the system before a doctor. The pacing system will then continuously change mode between DDD and VVI. The tracking of atrial activity causes irregular stimulation rates with high rates which are not needed. Undersensing of atrial activity will in this case even sometimes worsen the situation for the patient, since when each atrial activity is not sensed the pacemaker will not be properly inhibited with irregular heart rates as a result.

There are normally several months between the follow-up tests by a doctor and in case of a state of chronicle tachyarrhythmia or AF the above situation of continuous mode switching between DDD and VVI will remain for such a comparatively long time causing the patient considerable discomfort before the doctor reprograms the pacemaker in connection with testing of the system. Consequently, tracking of a fibrillating atrium has to be avoided and in the case of a chronic tachyarrhythmia or AF state, the VVI-R mode of operation is the preferred stimulation mode.

SUMMARY OF THE INVENTION

The present invention uses this knowledge to solve the above discussed problem related to a dual chamber pacing system when a tachyarrhythmia including AF of a patient changes from a paroxysmal to a chronicle state.

The above object is achieved in accordance with the present invention in a dual chamber pacing system that normally operates in an atrial synchronized mode, and that has a mode switch for switching the pacing mode to a non-atrial synchronized ventricle-stimulating mode in response to the detection of an initial tachyarrhythmia, and for switching the pacing mode back to the atrial synchronized mode in response to, or after a preset time following, the detection of ceased atrial tachyarrhythmia, and having a mode switch supervising unit with a counter for accumulating an amount of mode switches from a starting time, and supplying this accumulated amount to a comparator that compares the accumulated amount with a predetermined mode switch amount threshold, and wherein the supervising unit controls the mode switch to lock the pacing mode to the non-atrial synchronized ventricle-stimulating mode for a predetermined time period if the mode switch amount threshold is exceeded.

Thus an upper limit is set for the amount of allowed modes switches. When the amount threshold is reached the pacing mode will be locked to the pacing mode of non-atrial synchronized ventricular stimulation, VVI, for at least a predetermined time period, e.g. for a time of days or continuously. This will provide a smoother stimulation rate and more efficient function of the heart. The decreasing of unnecessary high rates will avoid heartbeats of low stroke volume and increase the blood flow to the heart muscle. The doctor will of course be alerted at the follow-up event about the actual situation of the patient from the stored event recordings.

In embodiments of the system according to the invention the counter directly counts the accumulated number of modes switches or the counter includes a clock for counting the accumulative time which the mode switch spends in a mode switching state to determine if and when the predetermined switch amount threshold is reached.

DESCRIPTION OF THE DRAWING

The single FIGURE is a flowchart illustrating the supervised mode switch function of the pacing system according to the invention.

DESCRIPTION OF THE PREFERRED EMBODIMENTS

The FIGURE is a block diagram schematically illustrating the principle structure and the function of the pacing system according to the invention. Block 2 represents the pacing, control and diagnostic electronics of the pacing system which at 14 is connected to an electrode system for delivery of stimulating pulses and sensing heart activity, e.g. atrial tachyarrhythmia including atrial fibrillation, for use for the control of the pacing. The pacing system also has an activity sensor 12 connected to the electronics block 2.

A mode switch 10 is connected to the electronics 2. The mode switch 10 is adapted to switch the pacing mode from an atrial synchronized pacing mode, like DDD-R, to a non-atrial synchronized ventricle stimulating mode, like VVI-R, in response to the detection, by block 2, of an atrial tachyarrhythmia-like an atrial fibrillation, and back to the DDD-R mode in response to or after a preset time of the detection of a ceased atrial tachyarrhythmia or atrial fibrillation.

A mode switch supervising unit, also contained in block 2, includes a counter for accumulating the amount of mode switches from a starting point, normally the last follow-up by a doctor, block 4. This accumulated amount is compared in comparator 6 with a predetermined mode switch amount threshold, block 8. The supervising unit is adapted to control the mode switch 10 to lock the pacing mode to the VVI-R mode for at least a predetermined time period in response to the accumulated mode switch amount exceeding the amount threshold.

The pacing system electronics 2 also includes a memory for storing pacing data, control and diagnostic data during the time between consecutive follow-ups at a hospital. The time between two consecutive follow-ups by a doctor can typically be six months. Events that are stored are for instance sensed and paced events recorded by the pacing system from the time when the event counter was last reset, i.e. the last follow-up, until the current programming procedure. The total time is the time elapsed since the last follow-up.

Examples of the statistics that can be calculated by the pacing system electronics are,
  percent of total time of counts paced in the atrium;
  percent of total time of counts paced in the ventricles;
  number of mode switch occurrences; and
  duration of mode switches.

One example of implementing the supervised mode switch function of the pacing system according to the invention involves counting the accumulated time, for instance by a real time clock, spent in the mode switching state for comparison with a predetermined mode switch amount threshold, as described above. The result of the comparison is supplied to the pacing system electronics 2 and when the threshold is exceeded the mode switch 10 will be activated and the stimulation mode locked to the VVI-R mode for at least a predetermined time period. The threshold amount can be e.g. one month in case of a follow-up period of six months. The threshold amount can alternatively be entered as a percentage of the follow-up period, in this case equal to 17%. This means that the mode switch supervising unit of the pacing system according to the invention is enabled if the pacing system has been in the mode switching state for a time of one month from the last follow-up, or 17% of the time between two consecutive follow-ups.

The invention claimed is:

1. A dual chamber pacing system comprising:
  a pulse generator and electrode arrangement adapted to interact with a subject to deliver pacing pulses to the subject;
  a control unit connected to the pulse generator for normally operating the pulse generator in an atrial synchronized pacing mode;
  said control unit being supplied with signals detected from the subject via the electrode arrangement and detecting, from said signals, if and when atrial tachyarrhythmia occurs;
  a mode switch connected to the control unit for, in response to detection of atrial tachyarrhythmia, switching the pacing mode to a non-atrial synchronized ventricle stimulating mode and to switch the pacing mode back to the atrial synchronized mode after, or at a predetermined time following, detection of cessation of the atrial tachyarrhythmia; and
  a mode switch supervising unit including a counter for accumulating an accumulated number of mode switches from a starting time, and a comparator to which said accumulated number is supplied, said comparator comparing said accumulated number to a predetermined mode switch number threshold, and said mode switch supervising unit controlling said mode switch to lock said pacing mode to said non-atrial synchronized ventricular stimulating mode for a predetermined time period if said mode switch number exceeds said mode switch number threshold.

2. A dual chamber pacing system as claimed in claim 1 wherein said counter directly counts said accumulated number of mode switches.

3. A dual chamber pacing system as claimed in claim 1 wherein said counter comprises a clock for counting an accumulated time which said mode switch spends in a mode switching state.

4. A dual chamber pacing system as claimed in claim 3 comprising a telemetry arrangement allowing follow-up tests by a physician, and wherein said amount threshold is a predetermined portion of a time between consecutive follow-up tests.

5. A dual chamber pacing system as claimed in claim 4 wherein said predetermined portion of the time between consecutive follow-up tests comprises multiple days.

6. A dual chamber pacing system as claimed in claim 1 wherein said mode switch supervising unit controls said mode switch to permanently change the pacing mode to said non-atrial synchronized ventricle stimulating mode if said mode switch amount exceeds said amount threshold.

* * * * *